United States Patent
Shaw et al.

(10) Patent No.: US 6,918,869 B2
(45) Date of Patent: Jul. 19, 2005

(54) SYSTEM FOR ADMINISTERING A COMBINATION OF THERAPIES TO A BODY LUMEN

(75) Inventors: William J. Shaw, Cambridge, MA (US); James Barry, Marlborough, MA (US); Paul J. Goll, Woodinville, WA (US); Maria Palasis, Wellesley, MA (US)

(73) Assignee: SciMed Life Systems, Maple Grove, MN (US)

( * ) Notice: Subject to any disclaimer, the term of this patent is extended or adjusted under 35 U.S.C. 154(b) by 0 days.

(21) Appl. No.: 10/307,917

(22) Filed: Dec. 2, 2002

(65) Prior Publication Data

US 2004/0106841 A1 Jun. 3, 2004

(51) Int. Cl.$^7$ .............................. A61N 5/00; A61B 9/22
(52) U.S. Cl. .......................................... 600/3; 604/890.1
(58) Field of Search ............................... 600/2–4, 8, 7, 600/685, 20; 623/1.13, 1.39, 1.42, 1.49, 901, 1.28, 1, 12, 1.16, 1.43; 606/194, 192, 195, 198, 20; 427/2.3, 2.28, 393.5, 430.1, 493, 5; 604/265, 103.02, 913, 508, 101.02, 103.05, 96.01, 103.11, 103.12, 500; 29/592; 376/158, 195, 201

(56) References Cited

U.S. PATENT DOCUMENTS

| | | | |
|---|---|---|---|
| 4,768,507 A | | 9/1988 | Fischell et al. |
| 5,059,166 A | | 10/1991 | Fischell et al. |
| 5,102,402 A | * | 4/1992 | Dror et al. .................. 604/265 |
| 5,139,496 A | | 8/1992 | Hed |
| 5,281,215 A | | 1/1994 | Milder |
| 5,292,321 A | * | 3/1994 | Lee ............................. 606/28 |
| 5,354,257 A | | 10/1994 | Roubin et al. |

(Continued)

FOREIGN PATENT DOCUMENTS

| | | |
|---|---|---|
| WO | WO 94/26205 | 11/1994 |
| WO | WO 00/76557 | 12/2000 |

OTHER PUBLICATIONS

Spear MA. Gene therapy of gliomas: receptor and transcriptional targeting. Anticancer Res. 1998 Sep–Oct;18(5A): 3223–31. Review.

Guha et al. Antisense ATM gene therapy: a strategy to increase the radiosensitivity of human tumors. Gene Ther. May 2000;7(10):852–8.

(Continued)

*Primary Examiner*—Max F. Hindenburg
*Assistant Examiner*—Nikita R. Veniaminov
(74) *Attorney, Agent, or Firm*—Jones Day

(57) ABSTRACT

The invention provides a system which comprises a medical device that delivers a combination of therapies. These therapies include the administration of radiation, biologically active materials, cryotherapy, and thermotherapy. The present invention is also directed to a method of treating body lumen surfaces using the system of the invention. A system is provided for delivering a biologically active material to a surface of a body lumen being exposed to a radioactive source. In one aspect, the system comprises an implantable medical device which has two opposing ends, each having a surface, and a middle portion. The two opposing ends comprise a biologically active material and the middle portion of the medical device is substantially free of any biologically active material. In another aspect, the system delivers a genetic material to a surface of a body lumen which is exposed to a radioactive source. Another system is provided for treating a surface of a body lumen in which the system comprises an implantable medical device which comprises a biologically active material and a device for applying a therapy source to the parts of the body lumen surface that are in contact with the opposing ends of the medical device. The therapy source may be a cryotherapy source or a thermotherapy source.

15 Claims, 6 Drawing Sheets

U.S. PATENT DOCUMENTS

| | | | | |
|---|---|---|---|---|
| 5,405,309 | A | * | 4/1995 | Carden, Jr. .................... 600/3 |
| 5,503,614 | A | * | 4/1996 | Liprie .......................... 600/7 |
| 5,789,018 | A | * | 8/1998 | Engelson et al. ............ 427/2.3 |
| 5,840,009 | A | | 11/1998 | Fischell et al. |
| 5,843,163 | A | | 12/1998 | Wall |
| 5,863,285 | A | * | 1/1999 | Coletti ......................... 600/3 |
| 5,871,437 | A | | 2/1999 | Alt |
| 5,899,898 | A | | 5/1999 | Arless et al. |
| 5,902,299 | A | * | 5/1999 | Jayaraman ................... 606/20 |
| 5,919,126 | A | | 7/1999 | Armini |
| 5,925,353 | A | | 7/1999 | Mosseri |
| 5,928,217 | A | * | 7/1999 | Mikus et al. ................ 604/530 |
| 5,971,979 | A | | 10/1999 | Joye et al. |
| 5,997,463 | A | * | 12/1999 | Cutrer .......................... 600/8 |
| 6,010,445 | A | | 1/2000 | Armini et al. |
| 6,051,019 | A | | 4/2000 | Dobak, III |
| 6,074,337 | A | * | 6/2000 | Tucker et al. ................. 600/2 |
| 6,096,070 | A | * | 8/2000 | Ragheb et al. ............. 623/1.39 |
| 6,099,455 | A | | 8/2000 | Columbo et al. |
| 6,129,757 | A | * | 10/2000 | Weadock ................... 623/1.39 |
| 6,139,536 | A | * | 10/2000 | Mikus et al. ................ 604/500 |
| 6,159,142 | A | | 12/2000 | Alt |
| 6,159,143 | A | | 12/2000 | Lennox |
| 6,168,619 | B1 | * | 1/2001 | Dinh et al. ................. 623/1.13 |
| 6,179,789 | B1 | | 1/2001 | Tu et al. |
| 6,231,516 | B1 | * | 5/2001 | Keilman et al. ............ 600/485 |
| 6,241,718 | B1 | | 6/2001 | Arless et al. |
| 6,248,057 | B1 | | 6/2001 | Mavity et al. |
| 6,273,908 | B1 | * | 8/2001 | Ndondo-Lay .............. 623/1.43 |
| 6,280,411 | B1 | * | 8/2001 | Lennox .................. 604/103.05 |
| 6,299,604 | B1 | * | 10/2001 | Ragheb et al. .............. 604/265 |
| 6,379,379 | B1 | | 4/2002 | Wang |
| 6,425,853 | B1 | | 7/2002 | Edwards |
| 6,468,297 | B1 | * | 10/2002 | Williams et al. ............ 607/113 |
| 6,491,617 | B1 | * | 12/2002 | Ogle et al. ..................... 600/3 |
| 6,497,647 | B1 | * | 12/2002 | Tucker ......................... 600/8 |
| 6,575,933 | B1 | * | 6/2003 | Wittenberger et al. . 604/101.02 |
| 6,656,216 | B1 | * | 12/2003 | Hossainy et al. .......... 623/1.13 |

OTHER PUBLICATIONS

Herrlinger et al. Transduction of human glioma cells by HSV/AAV hybrid vectors is increased by ionizing radiation. Proc. Am. Asso. for Cancer Res. Mar. 1997, 38:13 (#85).

Hehrlein et al. New concepts for radiative stents. " Conference Report: Recent Advances in Stents, Cardiovascular Radiation Therapy V and Restenosis Forum". Feb. 5–7, 2001, Washington D.C. by Gurberg et al. Chapter title: "Stenting and Radiation". (Http://www.medscape.com/Medscape/cardiology/2001/v05.n03/mc0606.grub/mc0606.grub–01.html).

Lojun et al. Murine intestinal crypt survival after combined taxol plus radiation exposure. Gynecol Oncol. 1996 Nov;63(2):180–3.

Steren et al. Taxol sensitizes human ovarian cancer cells to radiation. Gynecol Oncol. Feb 1993;48(2):252–8.

* cited by examiner

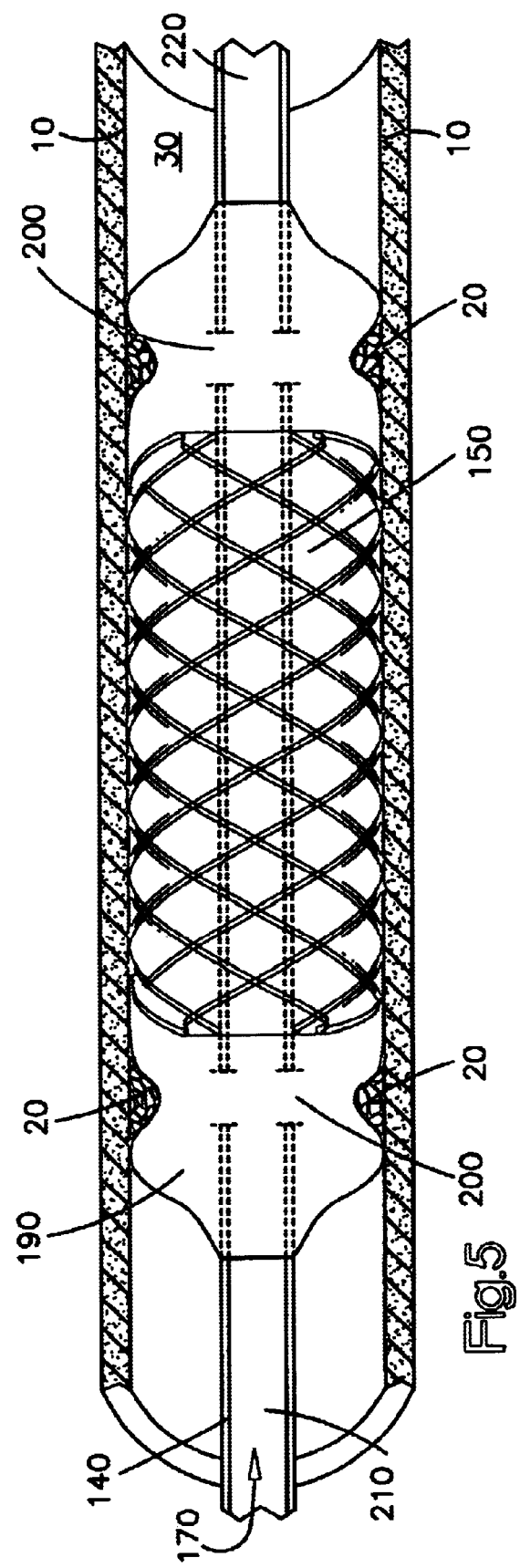

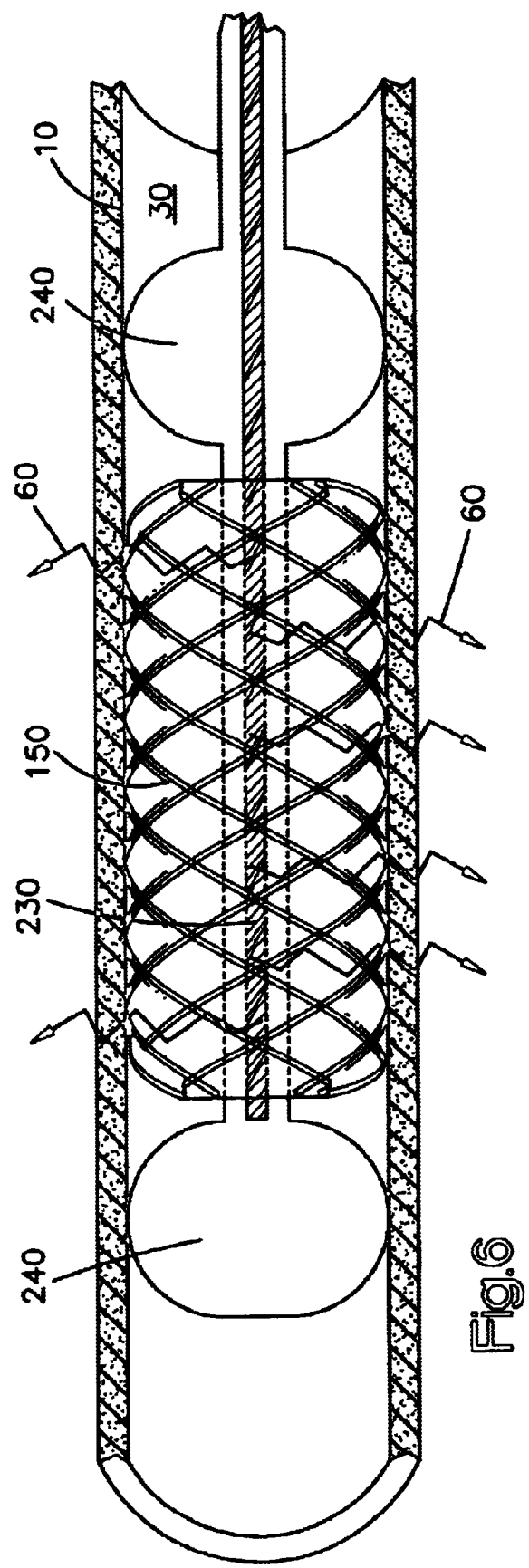

SYSTEM FOR ADMINISTERING A COMBINATION OF THERAPIES TO A BODY LUMEN

FIELD OF THE INVENTION

This invention relates generally to a system for delivering a biologically active material to a surface of a body lumen. More particularly, the invention is directed to a system comprising a medical device that delivers a combination of therapies. These therapies include the administration of radiation, biologically active materials, genetic materials, cryotherapy, and thermotherapy. Still further, the invention is directed to a method of treating a body lumen surface by preventing or treating restenosis or hyperplasia, using the system of the invention.

BACKGROUND OF THE INVENTION

Vascular interventions, including angioplasty, stenting, atherectomy and grafting are often complicated by undesirable effects. Exposure to a medical device which is implanted or inserted into the body of a patient can cause the body tissue to exhibit adverse physiological reactions. For instance, the insertion or implantation of certain catheters or stents can lead to the formation of emboli or clots in blood vessels. Similarly, the implantation of urinary catheters can cause infections, particularly in the urinary tract. Other adverse reactions to vascular intervention include endothelial and smooth muscle cell proliferation which can lead to hyperplasia, restenosis i.e. the re-occlusion of the artery, occlusion of blood vessels, platelet aggregation, and calcification. Treatment of restenosis often involves a second angioplasty or bypass surgery. In particular, restenosis may be due to endothelial cell injury caused by the vascular intervention in treating a restenosis. The drawbacks of such treatment, including the risk of repeat restenosis, are obvious.

For example, angioplasty involves insertion of a balloon catheter into an artery at the site of a partially obstructive atherosclerotic lesion. Inflation of the balloon is intended to rupture the intima and dilate the obstruction. About 20 to 30% of obstructions reocclude in just a few days or weeks. Eltchaninoff et al., *Balloon Angioplasty For In-Stent Restenosis*, 1998, *J. Am Coll. Cardiol.* 32(4): 980–984. Use of stents reduces the re-occlusion rate, however a significant percentage continues to result in restenosis. The rate of stenosis after angioplasty is dependent upon a number of factors including the length of the plaque. Stenosis rates vary from 10% to 35% depending the risk factors present. Further, repeat angiography one year later reveals an apparently normal lumen in only about 30% of vessels having undergone the procedure.

Restenosis is caused by an accumulation of extracellular matrix containing collagen and proteoglycans in association with smooth muscle cells which is found in both the atheroma and the arterial hyperplastic lesion after balloon injury or clinical angioplasty. Some of the delay in luminal narrowing with respect to smooth muscle cell proliferation may result from the continuing elaboration of matrix materials by neointimal smooth muscle cells. Various mediators may alter matrix synthesis by smooth muscle cells in vivo. A "cascade mechanism" has been proposed for restenosis. In this model, an injurious stimulus induces expression of growth-stimulatory cytokines such as interleukin 1 and tumor necrosis factor. Libby et al., *Cascade Model of Restenosis* 1992, Circulation 86(6): III-47–III52.

Various therapies have been attempted to treat or prevent restenosis. For example, it has been reported that, since oxidizing metabolites may induce chain reactions that may lead to restenosis, multivitamins having antioxidant properties (30,000 IU of beta carotene, 500 mg of vitamin C and 700 IU of vitamin E) and/or probucol (500 mg) were studied. They were administered twice daily for four weeks prior and six months after angioplasty, Tardif et al., 1997, *N. Engl. J. Med.* 337(6): 365–72. The antioxidant vitamins alone had no effect. Probucol did reduce the rate of restenosis after angioplasty by almost 50%. However, probucol has been removed from the U.S. market for reducing HDL cholesterol levels, and causing heart rhythm disturbances which might lead to dangerous arrhythmias.

Other therapies for treatment or prevention of restenosis that are under exploration include radiation (both $\beta$ and $\gamma$ emitters) delivery stents. Intracoronary irradiation during angioplasty and stent implantation to reduce the instances of restenosis have been studied. Limitations include, for example, handling stents filled with radioactive liquid (Re 188-radioactive rhenium). Further, studies show that this strategy may need to be tailored to stent design for proper distribution for the absorption and scattering of beta emitters. Amols et al., 1998, *Circulation* 98:2024–2029. Recently developed radiation delivery stents work on delivering radiation precisely at the location of stent deployment, either by placing a radioactive stent or by a secondary procedure of radiation delivery within the lumen of the stent following stent placement. This secondary procedure is usually carried out by placing a radioactive wire or a tube with radioactive seeds precisely within the stent and along the length of the stent. The radiation dose is administered such that it affects only the vessel wall. The treatment of restenosis with radiation has been shown to be effective although significant side effects have been observed, including late thrombosis, medial thinning and advential fibrosis.

Other methods for treatment or prevention of restenosis, include the administration of pharmaceuticals, such as anticoagulants and antibiotics, in or on medical devices, through systemic or local infusion. Various efforts and many state-of-the art stents that are undergoing clinical trials focus on the treatment of restenosis following stent placement. Drug delivery stents attempt to reduce restenosis by administering anti-inflammation drugs and cytotoxic drugs, which are used to prevent hyperplasia. Hormones may be delivered to control vessel hyperplasia near the stent. In many cases, anti-platelet or other anti-thrombotic agents may be incorporated to prevent thrombosis within the lumen of the stent.

In addition, gene therapy or protein therapy can be used for treatment or prevention of restenosis, cancer or hyperplasia through the administration of a biologically active material, such as nucleic acid or protein, to a subject who has restenosis, cancer or hyperplasia in whom prevention or inhibition of restenosis, cancer or hyperplasia is desirable. Genes expressing either cytotoxic or cytostatic proteins have been used. The major limitation in this approach has been the difficulty in getting enough of the gene into the afflicted tissue. Adenoviral vectors have improved the delivery of genes to tissues but only moderately.

For general reviews of the methods of gene therapy, see Goldspiel et al., 1993, *Clinical Pharmacy* 12:488–505; Wu and Wu, 1991, *Biotherapy* 3:87–95; Tolstoshev, 1993, *Ann. Rev. Pharmacol. Toxicol.* 32:573–596; Mulligan, 1993, *Science* 260:926–932; and Morgan and Anderson, 1993, *Ann. Rev. Biochem.* 62:191–217; May, 1993, *TIBTECH* 11(5):155–215). Methods commonly known in the art of recombinant DNA technology which can be used are described in Ausubel et al. (eds.), 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al. (eds.), 1994, Current Protocols in Human Genetics, John Wiley & Sons, NY.

One of the problems with the current technology, in particular radioactive stents, is that restenosis may still occur at the parts of the surface of the body lumen that are in contact with the ends of a stent. Closure or constriction of the vessels commonly occurs when the vascular cells proliferate around the ends of the stent. This is known as the "candy-wrapper effect", also known as edge restenosis or edge effect. Albiero et al., 2000, J. Invas. Cardiol. 12(8) :416–421; Latchem et al., 2000, Catheter Cardiovasc Interv. 51(4):422–429; Kim et al., 2001, J. Am. Coll. Cardiol. 37(4):1026–1030. A schematic diagram describing this effect is show in FIG. 1. FIG. 1 shows a cross section of a body lumen with a radioactive stent implant where restenosis occurred at the opposing ends of the stent. The surface 10 of a body lumen 30 at the ends of the implanted stent 40 is surrounded by hyperproliferating tissues 20. This appearance is similar to a candy with a wrapper and thus the name "candy-wrapper effect". A cause for some types of hyperplasia is that when a body lumen is treated with radiation, the radioactive source is usually targeted towards the center of the stent where the original lesion was situated. In an effort to minimize extraneous radiation to healthy vessel tissue, radiation is targeted towards the center. Hence, restenosis may still occur at the edge of the stent due to a lower dosage of radiation at the ends. The underlying mechanism for this effect is that the radiation dosage at the ends is at a level such that it stimulates cell growth as opposed to stopping it. Clearly, there remains a great need for therapies directed to the prevention and treatment of restenosis and related disorders.

Therefore, there is a need for a system to provide treatment of a body lumen particularly where it is in contact with the ends of a medical device such as a stent and in particular preventing intimal hyperplasia and smooth muscle cell proliferation which cause stenosis or restenosis of the body lumen.

Citation of references hereinabove shall not be construed as an admission that such references are prior art to the present invention.

SUMMARY OF THE INVENTION

The present invention is aimed at using an implantable medical device to effect a desired treatment, which is often, but not necessarily, the prevention of restenosis. Specifically, the invention is aimed at reducing the incidence of restenosis by exposing a potential restenosis site to treatment by, e.g. radiation, biologically active materials, genetic materials, cryotherapy and thermotherapy. The system of the present invention was designed to provide a therapy which may include any of the above treatments in combination.

In one embodiment of the present invention, a system is provided for delivering a biologically active material to a surface of a body lumen exposed to a radioactive source. The radioactive source can be, but need not be, incorporated into the medical device. This system comprises an implantable medical device which has two opposing ends, each having a surface, and a middle portion and a surface. At least one biologically active material is applied to at least one end of the device. An end is a portion of the device at the terminus of the device that is no more than about 25% of the total length of the device. The middle portion of the medical device is substantially free of any biologically active material. In another embodiment, a system comprises an implantable medical device comprises at least one biologically active material coated onto the surface of the device.

Furthermore, in yet another embodiment, the present invention provides a system for delivering a biologically active material to a surface of a body lumen exposed to a radioactive source. The system comprises an implantable medical device having two opposing ends and a middle portion and a surface. At least one biologically active material is applied to the ends of the medical device. The radioactive source is applied to the middle portion of the medical device and the end portions of the medical device are substantially free of direct exposure to the radiation source. In a specific embodiment, the biologically active material is applied to the middle portion of the medical device.

In another embodiment, a system is provided for treating a surface of a body lumen in which the system comprises an implantable medical device which has two opposing ends and a middle portion. The medical device further has a surface which is capable of being placed in contact with at least a part of the body lumen. The system comprises at least one biologically active material applied to the medical device. The system further comprises a device for applying a therapy source to the body lumen surface. The therapy source may be a cryotherapy source or a thermotherapy source. The therapy source can be provided through a balloon catheter which may be located along the entire length of the implantable medical device. In another embodiment, the biologically active material is provided through a balloon catheter. In a specific embodiment, the balloon may be located at each of the ends of the implantable medical device, providing the biologically active material to each of the ends of the implantable medical device.

In yet another embodiment, a system is provided for treating a surface of a body lumen exposed to a radioactive source. The system comprises an implantable medical device having two opposing ends and a middle portion and a surface. The two opposing ends may be placed in contact with at least a part of the body lumen surface. The system further comprises a device for applying a therapy source to the body lumen surface. Also, the therapy source may be a cryotherapy source or a thermotherapy source. The therapy source can be provided through a balloon catheter which may be located along the entire length of the implantable medical device. In another embodiment, the biologically active material is provided through a balloon catheter located at each of the ends of the implantable medical device.

Moreover, it is an object of the present invention to provide a system for delivering a genetic material to a surface of a body lumen exposed to a radioactive source. The system comprises a medical device having two opposing ends, and a middle portion. At least one genetic material is applied to the medical device. The genetic material may be applied to the entire length of the medical device or just to the ends so that the middle portion is substantially free of any biologically active material, including the genetic material.

BRIEF DESCRIPTION OF THE DRAWINGS

FIG. 5 is a cross-sectional view showing the surface 10 of a body lumen 30 in which hyperplasia is prevented using an embodiment of the invention comprising a drug coated stent 150 in combination with a balloon catheter 190 that delivers a cryotherapy or thermotherapy source.

FIG. 6 is a cross-sectional view showing the surface 10 of a body lumen 30 in which hyperplasia is prevented using an embodiment of the invention comprising a stent 150 in which a radioactive wire 230 is placed in the center providing radiation 60. A balloon is located at the ends of the stent 150 that delivers a biologically active material, cryotherapy or thermotherapy source.

DETAILED DESCRIPTION OF THE INVENTION THE SYSTEM OF THE INVENTION

The system of the present invention comprises a medical device having two opposing ends and a middle portion and a surface. Such devices include but are not limited to catheters, implantable vascular access ports, stents, central venous catheters, prosthetic seeds, catheters, (arterial, venous, non-vascular and vascular) grafts, and aneurysm filing coils.

Figure 1:
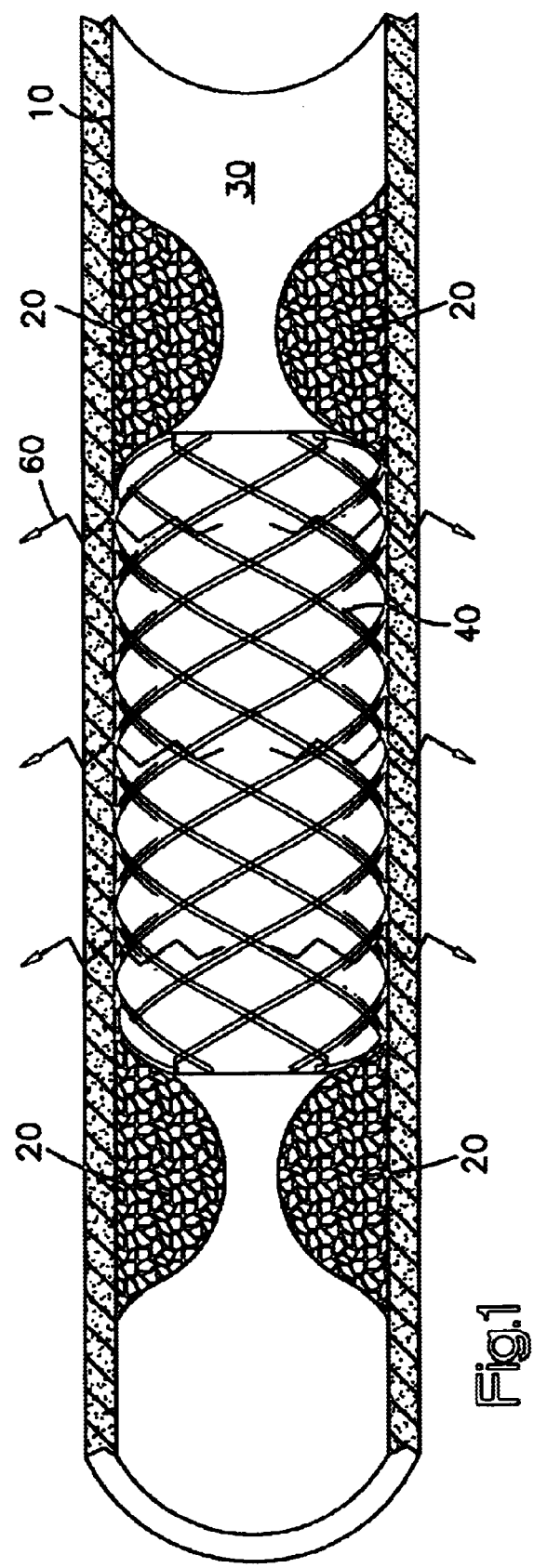
FIG. 1 is a cross-sectional view showing the "candy-wrapper effect" of a surface 10 of a body lumen 30 in which restenosis occurred with hyperproliferating tissues 20 at the surface 10 of the body lumen 30, at or near the ends of a radioactive stent 40 which emits radioactive energy 60.

The present invention is useful in treating surfaces of body lumens, particularly in the prevention and treatment of restenosis or hyperproliferating tissue in body lumens. For instance, as shown in FIG. 1, even though a stent 40 has been inserted in the body lumen 30 to prevent restenosis, such undesired restenosis 20 can nonetheless occur, particularly at or near the ends of the stent 40, when the body lumen is exposed to a radioactive source. This effect is the "candy-wrapper effect", also known as edge restenosis or edge effect, mentioned above. The claimed system can be effective in preventing or minimizing such effect.

Figure 2:
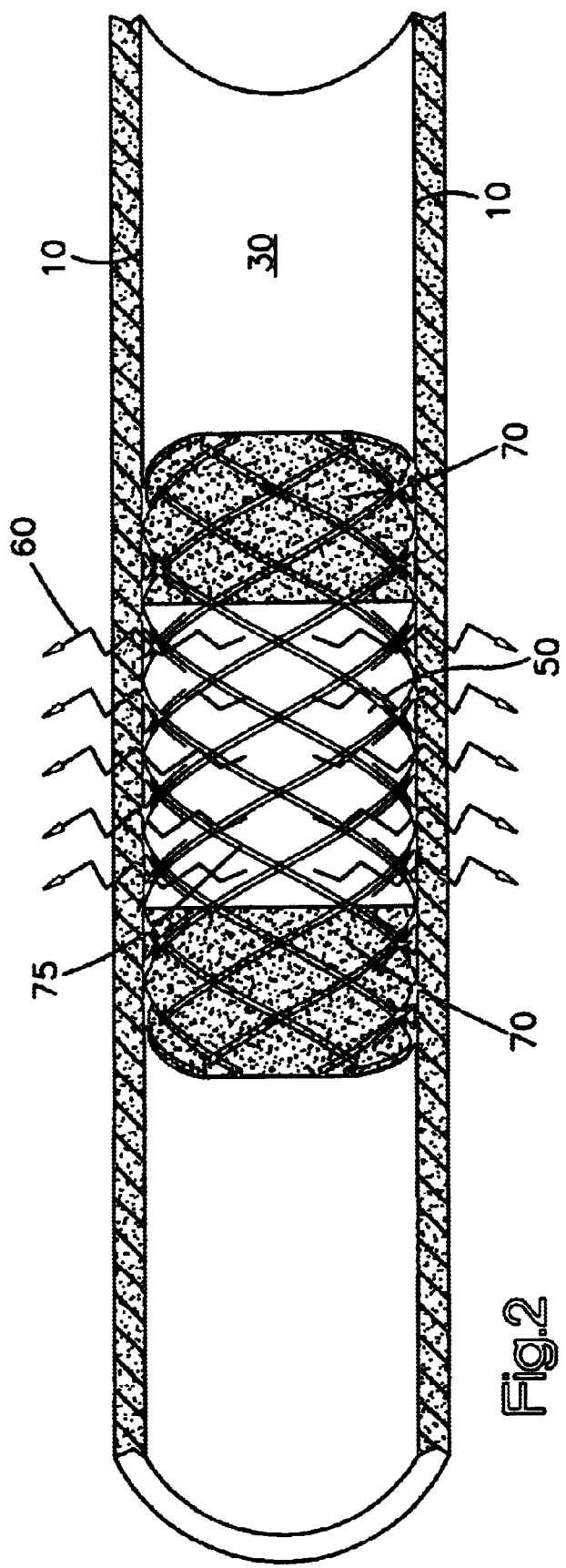
FIG. 2 is a cross-sectional view showing the surface 10 of a body lumen 30 in which hyperplasia is prevented using one embodiment of the invention involving a stent 50 which has drug coated ends 70 and a middle portion, 75 which applies a radioactive source 60 to the surface of the body lumen.

An embodiment of a system of the present invention is illustrated in FIG. 2. FIG. 2 shows a cross-sectional view of a body lumen 30 in which an expandable stent 50 has been implanted at a site where hyperplasia or restenosis is to be prevented. This system comprises a flexible elongated stent 50 whose middle portion is formed from a radioactive material which exposes the surface of the body lumen 30 to radiation 60. In alternative embodiments, the radioactive source could be supplied by another device such as a catheter or radioactive seeds placed inside the stent lumen, using a delivery catheter. In a specific embodiment, radiation may be administered at the middle portion of the stent and the ends, which comprise a biologically active substance, are substantially free of direct exposure to radiation. In another embodiment, radiation may be directly administered to the entire length of the stent, even at the ends, of the stent, as long as each of the ends comprises a biologically active material.

In an embodiment, the opposing ends of the stent 70 comprise a biologically active material. However, the middle portion is substantially free of any biologically active material. The biologically active material can be incorporated into the ends 70 of the stent 50 by various devices known to those skilled in the art. Such techniques include coating the ends 70 with a composition containing the biologically active material or chemically bonding the biologically active material to the surface of the ends 70. In a specific embodiment, the biologically active agent may be delivered through a separate catheter. For example, the delivery catheter for the radioactive stent may have one or two drug delivery balloons along the shaft. Alternatively, a systemically delivered agent may assist in prevention of restenosis at the ends.

An example of the ends of a device is illustrated in FIG. 2 with the opposing ends of the stent 70 as the ends. The end of the device is considered to be that portion at a terminus of the medical device that is no more than about 25% of the total length of the device. Thus, the lengths of each of the two opposing ends that comprises the biologically active material are about 1–25% of the full length of the medical device. Preferably the ends are each about 5–15% of the total length or more preferably they are about 5–10% of the total length.

Figure 3:
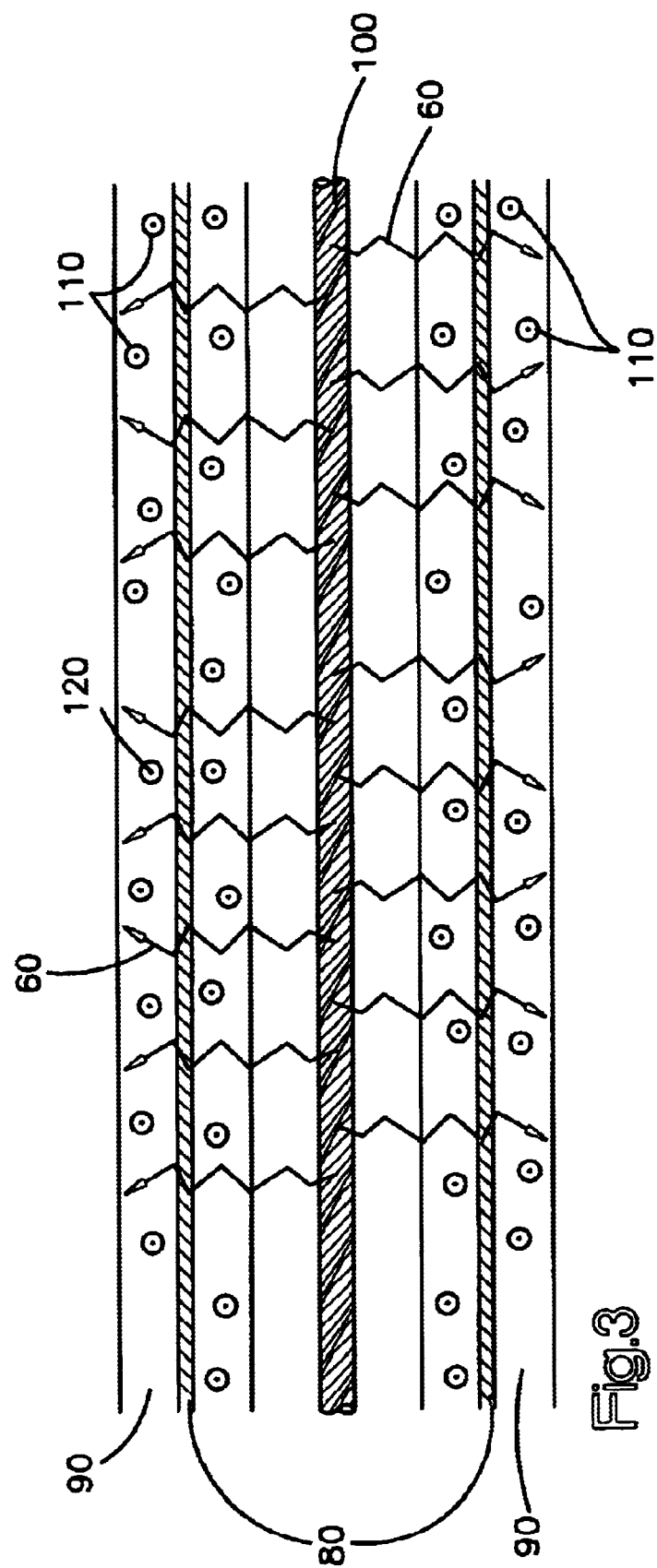
FIG. 3 is a schematic diagram of a magnified cross-section of a portion of stent 50 covered with a biologically active material 70 that is shown in FIG. 2. Struts 80 are covered with a coating 90 which comprises biologically active material 120 within capsules 110.

FIG. 3 shows a magnified cross-section of a portion of stent 50 of FIG. 2. Struts 80 of the stent 50 are covered with a coating 90 comprising of biologically active material which may be contained in capsules 110 such as liposomes. Radiation 60 is provided by a radioactive source 100 which is placed near the stent struts 80. The radiation 60 triggers the release of the biologically active material 120 from the capsules 110. In another embodiment, the release of the biologically active material need not be triggered by the radiation. The biologically active material is released upon application of the radioactive source.

In another embodiment, the biologically active material 120 is a genetic material. Useful genetic material includes nucleic acid molecules such as DNA or RNA sequences having a therapeutic effect after being taken up by a cell. Other examples are discussed infra. In this embodiment, the genetic material may be present along the entire length of the implantable device including the middle portion or located at certain parts of the device.

Figure 4:
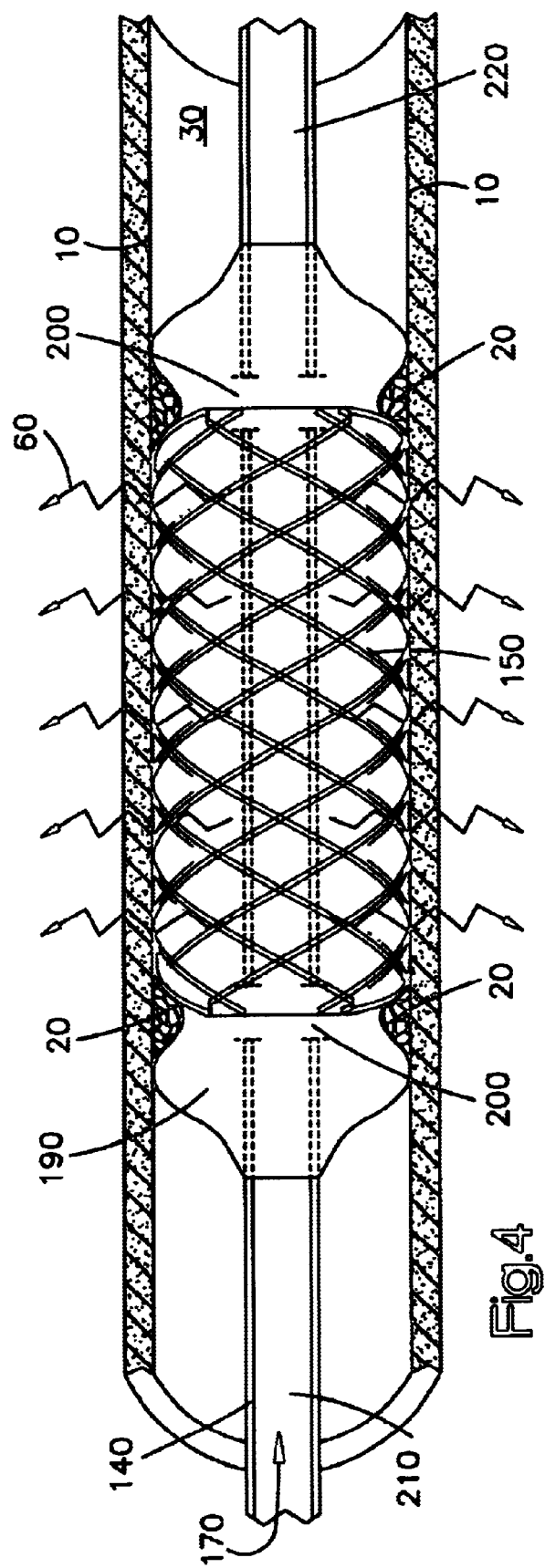
FIG. 4 is a cross-sectional view showing the surface 10 of a body lumen 30 in which hyperplasia is prevented using the system of the invention comprising a stent 150 formed of a radioactive material in combination with a balloon catheter 190 that delivers a cryotherapy or thermotherapy source to the body lumen.

Another embodiment of the system of the present invention is illustrated in FIG. 4. FIG. 4 shows a cross-sectional view of a body lumen 30 in which a radioactive stent 150 has been implanted. The stent 150 is surrounded on either end by target regions 20 which are sites of possible restenosis or hyperplasia in the body lumen surface 10. Stent 150 may be made radioactive by various methods known in the art such as incorporating into or coating onto the stent a radioactive material. In an alternative embodiment, the surface 10 of the body lumen 30 can be irradiated by a separate radioactive source, such as a catheter. Also in this embodiment, a device such as a balloon catheter 190 is introduced into the body lumen 30 to deliver a cryotherapy or thermotherapy source to the target regions 20. The catheter 190 may be any type of catheters described infra, that can deliver cryotherapy or thermotherapy sources. Cryotherapy and thermotherapy sources are also described infra.

In this embodiment, the balloon 190 has a proximal end 170, a distal end 220 and a guide wire (not shown) and a lumen 210 for inflating the balloon and delivering the cryotherapy or thermotherapy source. An inflatable balloon 190 is disposed on the catheter 140. The catheter 140 is positioned within the lumen of stent 150, so that the balloon 190 is in contact with the targeted areas 20 in the body lumen. A cryotherapy source, e.g. a cold fluid, or a thermotherapy source, e.g. a hot liquid, is delivered through the lumen 210 to the interior of the balloon 190 through openings 200, which are located near the ends of the stent. Specifically, the cryotherapy source travels along the lumen 210 and fills the balloon 190 at openings 200. Openings 200 are positioned such that they are near the ends of the stent and target areas 20. As the balloon 190 is inflated, the outer wall of the balloon contacts those parts of the surface of the body lumen that are in contact with the opposing ends of the medical device. In this manner, the cryotherapy or thermotherapy source is applied to those parts of the body lumen surface that are in contact with the ends of the stent. Cryotherapy and thermotherapy can be provided in other manners as well. For example, it may be created within the balloon by a small heater (such as radio frequency antennas of Boston Scientific Corporation) or cooler (having Peltier effect) or nitrogen nozzles used by Cryocathe and Novoste Corporation. Alternatively, the balloon wall may have pores or openings near the ends of the stent so that the cryotherapy or thermotherapy or pharmaco-therapy source can be applied directly to the surface of the body lumen in contact with the ends of the stent.

Yet another embodiment of a system of the present invention is illustrated in FIG. 5. FIG. 5 shows a cross-sectional view of a body lumen 30 in which a stent 150, coated with a biologically active material has been implanted. The stent is surrounded by exemplary target regions 20 where hyperplasia or restenosis is to be prevented or treated. The target region can be along the entire body lumen surface in contact with the stent or located at the body lumen surface at the ends of the stent. Stent 150 can be any stent or medical devices that has two opposing ends and a middle portion. The biologically active material may be any therapeutics described infra. The biologically active material may be coated onto the stent by any methods known in the art, some of which are described infra. The system also includes a balloon catheter 190 or other device for applying a cryotherapy or thermotherapy or pharmaco-therapy source to the surface of the wall of the body lumen that is in contact with the stent 150. The catheter 140 applies these therapy sources to the target regions 20 and those parts of the body lumen surface in contact with the stent.

Yet another embodiment of a system of the present invention is illustrated in FIG. 6. FIG. 6 shows a cross-sectional view of a body lumen 30 in which neither the radioactive source nor a second source, which may be biologically active material, cryotherapy source or thermotherapy source, is on stent 150. A delivery catheter provides the radioactive source to the center of stent 150 and the delivery catheter or a separate catheter may have one or more balloons for delivering a biologically active material, cryotherapy source or thermotherapy source, along the shaft.

Medical Devices that are Suitable for the Invention

Examples of medical devices that are suitable for use in the system of this invention include any device having opposing ends and a middle portion. These devices are not only for the treatment of stenosis. Adjunct therapy of radiation and biologically active material may provide novel treatments for various diseases such as hyperproliferative diseases including cancer, which may not result from treatment of stenosis. Devices that are suitable for the present invention include without limitation catheters, guide wires, balloons, filters (e.g., vena cava filters), stents, stent grafts, a commercial synthetic graft, prosthetic seed, dialysis shunt, aneurysm coil, a biological vascular or non-vascular graft, filters, implants, and angioplasty devices.

Devices which are particularly suitable include vascular or non-vascular stents such as self-expanding stents and balloon expandable stents. Examples of self-expanding stents useful in the present invention are illustrated in U.S. Pat. Nos. 4,655,771 and 4,954,126 issued to Wallsten and U.S. Pat. No. 5,061,275 issued to Wallsten et al. Examples of appropriate balloon-expandable stents are shown in U.S. Pat. No. 4,733,665 issued to Palmaz, U.S. Pat. No. 4,800,882 issued to Gianturco and U.S. Pat. No. 4,886,062 issued to Wiktor. Examples of filters that are useful in this present invention include, e.g., those described in International Application No. WO 96/17634 and International Application No. WO 96/12448. Examples of suitable grafts are described in U.S. Pat. Nos. 5,509,931, 5,527,353, and 5,556,426.

Medical devices that are useful in the present invention can be made of any biocompatible material suitable for medical devices in general which include without limitation natural polymers, synthetic polymers, ceramics and metallics.

The polymer(s) useful for forming the medical device should be ones that are biocompatible and avoid irritation to body tissue. They can be either biostable or bioabsorbable. Polymers that may be used in the present invention may be hydrophilic or hydrophobic, and is selected from the group consisting of polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as PVA, polyvinyl ethers, polyvinyl aromatics, polyethylene oxides, glycosaminoglycans, polysaccharides, polyesters including polyethylene terephthalate, polyacrylamides, polyethers, polysulfones, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof as well as other biodegradable, bioabsorbable and biostable polymers and copolymers.

Other polymers which can be used include ones that can be dissolved and cured or polymerized on the medical device or polymers having relatively low melting points that can be blended with therapeutic agents. Such suitable polymers include polyolefins, polyamides, polyisobutylene, ethylene-alphaolefin copolymers, acrylic polymers and copolymers, vinyl halide polymers and copolymers such as polyvinyl chloride, polyvinyl ethers such as polyvinyl methyl ether, polyvinylidene halides such as polyvinylidene fluoride and polyvinylidene chloride, polyacrylonitrile, polyvinyl ketones, polyvinyl aromatics such as polystyrene, polyvinyl esters such as polyvinyl acetate; copolymers of vinyl monomers, copolymers of vinyl monomers and olefins such as ethylene-methyl methacrylate copolymers, acrylonitrile-styrene copolymers, ABS resins, polycarbonates, acrylonitrile butadiene, styrene copolymers, ethylene vinyl-acetate, thermoplastic elastomers, ethylene-vinyl acetate copolymers, polyamides such as Nylon 66 and polycaprolactone, alkyd resins, polycarbonates, polyoxymethylenes, polyimides, polyesters, epoxy resins, rayon-triacetate, cellulose, cellulose acetate, cellulose butyrate, cellulose acetate butyrate, cellophane, cellulose nitrate, cellulose propionate, cellulose ethers, carboxymethyl cellulose, collagens, chitins, polylactic acid, polyglycolic acid, and polylactic acid-polyethylene oxide copolymers.

More preferably for medical devices which undergo mechanical challenges, e.g. expansion and contraction, are polymers selected from elastomeric polymers such as silicones (e.g. polysiloxanes and substituted polysiloxanes), polyurethanes, thermoplastic elastomers, ethylene vinyl acetate copolymers, polyolefin elastomers, polyisobutylene and its copolymers, and EPDM rubbers.

Other polymers that are useful as materials for medical devices include without limitation dacron polyester, poly (ethylene terephthalate), polycarbonate, polymethylmethacrylate, polypropylene, polyalkylene oxalates, polyvinylchloride, polyurethanes, polysiloxanes, nylons, poly(dimethyl siloxane), polycyanoacrylates, polyphosphazenes, poly(amino acids), ethylene glycol I dimethacrylate, poly(methyl methacrylate), poly(2-hydroxyethyl methacrylate), polytetrafluoroethylene poly (HEMA), polyhydroxyalkanoates, polytetrafluorethylene, polycarbonate, poly(glycolide-lactide) co-polymer, polylactic acid, poly(ε-caprolactone), poly(β-hydroxybutyrate), polydioxanone, poly(γ-ethyl glutamate), polyiminocarbonates, poly(ortho ester), polyanhydrides, alginate, dextran, chitin, cotton, polyglycolic acid, polyurethane, or derivatized versions thereof, i.e., polymers which have been modified to include, for example, attachment sites or cross-linking groups, e.g., RGD, in which the polymers retain their structural integrity while allowing for attachment of molecules, such as proteins, nucleic acids, and the like.

Furthermore, although the invention can be practiced by using a single type of polymer to form the medical device, various combinations of polymers can be employed. The appropriate mixture of polymers can be coordinated with biologically active materials of interest to produce desired effects when incorporated into a medical device.

Metallic materials that can be used to make the medical device used in the present invention include metals and alloys based on titanium (such as nitinol, nickel titanium alloys, thermo-memory alloy materials), stainless steel, tantalum, nickel-chrome, or cobalt-chromium (such as Elgiloy® and Phynox®). Metallic materials also include clad composite filaments, such as those disclosed in WO 94/16646. Examples of ceramic materials include ceramics of alumina and glass-ceramics such as Macor®.

Metallic materials may be made into filaments and then woven to form a network of metal mesh. Polymer filaments may also be used together with the metallic filaments to form a network mesh. If the network is made of metal, the intersection may be welded, twisted, bent, glued, tied (with suture), heat sealed to one another; or connected in any manner known in the art.

Sources of Radiation

The radioactive sources that are suitable for use in the invention would be known to the skilled artisan. Temporary or permanent radioactive sources may be used. For instance, there are many ways to apply the radioactive source. The medical device may be composed of a radioactive material. For example, the radioactive material may be applied as a coating or covering. Also, the radioactive source may be supplied from a source other than the medical device itself, e.g., radioactive particles can be tethered to polymers and delivered locally via a device. Such polymers include natural polymers such as protein, oligonucleotides, DNA, RNA, etc. In addition, radioactive fluid may be injected into a catheter or balloon which is placed at the center of the medical device. Also, radioactive wire may be inserted at the center of the medical device. Furthermore, non-radioactive stent may be exposed to radiation in a machine and then implanted as a radioactive stent.

When the medical device is comprised of a radioactive material, the medical device can be formed by alloying a radioactive material into the metal from which the stent is made. The radioactive material can also be alloyed or woven into the stent struts. For example, phosphorus 32, a 14.3 day half-life beta emitter, could be alloyed into steel which could be used for the stent struts. Also, as described in U.S. Pat. No. 6,010,445, the medical device can be alloyed with an activatable element (precursor isotope). Neutron activation of the medical device material with the incorporated precursor isotope provides a radioactive medical device. The neutron activation may take place in a nuclear reactor prior to implant. Such activatable metals and metal alloys include iron, chromium, stainless steel, nitinol, rhenium-185, rhenium-187, rhenium alloy, tungsten-186. Alternatively, the radioactive material can be coated onto the surface of the medical device or be placed inside the medical device.

When the radioactive source is supplied from a source other than the medical device, a catheter can be used to apply the radiation treatment to the body lumen. Such radioactive sources include seeds, radioactive wires, radioactive fluids, radioactive coatings, radioactive balloons, and radioactive elements bound to a substrate, such as a polymer.

The radioactive source may be a radioactive isotope. The radioisotope used for this purpose may be an alpha, beta, or gamma emitter or x-radiation. The half-life of the radioisotope would ideally be between 10 hours and 100 days. A preferred x-ray emitter can be a beta emitting isotope such as vanadium 48 which has a half-life of 16 days and only 8% of its emitted energy is from gamma radiation. The ideal attribute of a beta emitter is that the radiation does not travel very far into human tissue. Thus only the tissue in close proximity to the radioisotope will be affected. Furthermore only moderate levels of radiation are desired since it is known that very high levels can cause injury to nonproliferating tissues.

Applicable Biologically Active Materials

The biologically active materials which can be used in the invention can be any therapeutic substances such as those which reduce or prevent adverse physiological reactions from vascular interventions. The biologically active materials can be of various physical states, e.g., molecular distribution, suspensions, crystal forms or cluster forms. The biologically active material used in the present invention may be bound to microspheres or contained within microcapsules (e.g. liposomes) or iodinized oils as the carrier. In one embodiment, the biologically active material can be activated by radiation.

Suitable biologically active materials include in general, antiplatelet agents, anti-coagulant agents, anti-cancer agents, antimitotic agents, cytotoxic agents, antioxidants, antimetabolite agents, and anti-inflammatory agents. Antiplatelet agents can include drugs such as aspirin and dipyridamole. Aspirin is classified as an analgesic, antipyretic, anti-inflammatory and antiplatelet drug. Dipyridamole is a drug similar to aspirin in that it has anti-platelet characteristics. Dipyridamole is also classified as a coronary vasodilator. Anticoagulant agents can include drugs such as protamine, hirudin and anticoagulant protein. Anti-cancer agents can include drugs such as taxol, paclitaxel, and its analogs or derivatives. Antioxidant agents can include probucol and anti-proliferative agents can include nitric oxide (NO) and drugs such as amlodipine and doxazosin. Antimitotic agents and antimetabolite agents can include drugs such as methotrexate, azathioprine, vincristine, vinblastine, 5-fluorouracil, adriamycin, mutamycin, and sirolimus. Antibiotic agents can include penicillin, cefoxitin, oxacillin, tobramycin, and gentamycin. Preferably, the biologically active material is activated by radiation.

Other examples of biologically active materials that can be used in accordance with the present invention include, but are not limited to, anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, and acetylsalicylic acid; anti-inflammatory agents such as glucocorticoids, betamethasone, dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants such as D-Phe-Pro-Arg chloromethyl keton, an RGD peptide-containing compound, antithrombin compounds, platelet receptor antagonists, anti-thrombin antibodies, anti-platelet receptor antibodies, aspirin, prostaglandin inhibitors, platelet inhibitors and tick antiplatelet peptides; vascular cell growth promotors such as growth factors, including FGF, HGF, and VEGF, growth factor receptors, transcriptional activators, and translational promotors; vascular cell growth inhibitors such as antiproliferative agents, growth factor inhibitors, growth factor receptor antagonists, transcriptional repressors, translational repressors, replication inhibitors, inhibitory antibodies, antibodies directed against growth factors, cell cycle inhibitors such as CD inhibitors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; and agents which sensitize cells to radiation.

Biologically active materials including cells may be used in the present invention as described below. These cells can be of human origin (autologous or allogeneic) or from an animal source (xenogeneic). These cells can be genetically engineered containing an exogenous nucleic acid comprising a nucleotide sequence encoding a gene such as thymidine kinase, retinoblastoma, p53, CDKN2, MTS-1, P16 (INK4a), p21, fasL, VEGF and HFG; and genes which sensitize cells to radiation. Other genetic material that are suitable for use in the invention are discussed infra. The delivery media can be formulated as needed to maintain cell function and viability. Various cell types may be used in the present invention, including but not limited to, embryonic stem cells, multi-potent stem cell of monocyte-macrophage, hematopoietic cells, lymphocytes, neutrophil system, megakaryocytes, erythrocytes, bone marrow, stromal cells, hepatocytes, epithelial cells, fibroblasts, endocrine cells, intestinal cells, pancreatic islet cells, thyroid cells, pituitary cells.

Negatively charged biologically active materials that may be used as a therapeutic in the present invention can be any biologically active materials that will associate with the positively charged moieties on the derivatized polymer at or below about a physiological pH, which is preferably about 7.4, and that will be substantially released therefrom at or above a physiological pH. Such negatively charged therapeutic agents include, but are not limited to nucleic acids such DNA, cDNA, RNA, antisense DNA or RNA, nucleotides, proteins, oligopeptides which are discussed infra.

Also, a biologically active material may be encapsulated by liposomes before they are incorporated into or onto the medical device. These liposomes are preferably ruptured by radiation so that the biologically active materials may be released upon radiation treatment. The encapsulated biologically active materials useful in the present invention may be prepared in a number of ways known in the art. For example, microencapsulation techniques for the preparation of microcapsules having a wall or membrane of polymeric material are described in literature such as "Microencapsulation and Related Drug Processes" by P. D. Deasy, Marcel Dekker Inc. New York (1984).

The method of incorporating the biologically active material into the medical device such as stents encompasses any of the methods known in the art, including the use of graft coverings, coatings comprising hydrogels or other polymers, adhesives, and reservoirs, etc. Alternatively, the biologically active material may be incorporated onto the medical device through chemical bond or covalent bond. Preferably, the biologically active material is incorporated onto the device by applying a coating or multiple coatings of a composition each containing the same or different biologically active materials. The biologically active material may be incorporated onto or into the stent with or without mixing with a polymer.

The polymer used in the coating composition is preferably capable of containing a substantial amount of biologically active materials. Polymers that are suitable in a coating composition includes, without limitation, polyurethane dispersions (BAYHDROL®, etc.) and acrylic latex, protein polymer, fibrin, collagen and derivatives thereof, polysaccharides such as celluloses, starches, dextrans, alginates and derivatives of these polysaccharides, an extracellular matrix component, hyaluronic acid, or another biological agent or a suitable mixture of any of these, for example. In one embodiment of the invention, the preferred polymer is polyacrylic acid, available as HYDROPLUS® and SiBs styrene (Boston Scientific Corporation, Natick, Mass.), and described in U.S. Pat. No. 5,091,205. In a most preferred embodiment of the invention, the polymer is a copolymer of polylactic acid and polycaprolactone.

The particular amount of the preparation to be applied to the device can be easily determined empirically by comparing devices with different amounts of the drug coated thereon and determining the efficacy of each. Also, one skilled in the relevant art would also be in a position to easily evaluate the efficacy of a device.

Moreover, more than one coating of the drugs, can be applied to the surface of a medical device. The concentration or loading of biologically active material in the coating may be varied according to the therapeutic effects desired.

Generally, the coating may contain 10–100% by weight or preferably 30–100% by weight of the biologically active material. Most preferably, 45–100% by weight of the biologically active material should be incorporated in the coating.

The coating composition can be applied by such methods as dipping, casting, extruding, vacuum deposition or spray coating. The coating with the biologically active materials may be applied to the inside or outside surface of the medical device. Spray coating the composition onto the medical device is preferred since it permits the thickness of the coating to be readily adjusted. The thickness of the coating can range from about 0.1 to about 100 microns. Preferably, this layer is about 1 to about 5 microns; 15 to 50 microns. Since different coating thicknesses can be readily achieved by adjusting the number of spray cycles, spray coating the medical device is preferred. Typically, an airbrush such as a Badger Model 150 (supplied with a source of pressurized air) can be used to coat the device. If a significant amount of surface area is to be coated, it may be preferable to place the device in a rotating fixture to facilitate the coverage of the device surface.

Moreover, several coatings of different compositions may be used so that more than one biologically active material and/or polymer may be incorporated onto the medical device. The placement of the different layers may be determined by the diffusion or elution rates of the biologically active material involved as well as the desired rate of delivering it to the body tissue. In one embodiment, the first coating layer contains a higher dose of biologically active material and the subsequent coating layers contain a lower dose of a biologically active material. This gradient provides replenishment of biologically active material from the first coating layer to the subsequent coating layers, thereby allowing the biologically active material to be released slowly over time.

After application of the coating, the polymer can be cured to produce a polymer matrix containing the biologically active material and the solvent evaporated by any method known in the art. Certain polymers, such as silicon, can be cured at relatively low temperatures, (e.g. room temperature) in what is known as a room temperature vulcanization process. The time and temperature of heating will of course vary with the particular polymer, drugs, solvents and/or crosslinkers used. One of skill in the art is aware of the necessary adjustments to these parameters. Also, the devices may be cured after the last layer of coating has been applied.

Furthermore, to prepare a stabilized coatings used in this invention, the medical devices can be exposed to a low energy, relatively non-penetrating energy source such as gas plasma, electron beam energy, or corona discharge after they are covered with at least a layer of a drug-releasing coating. In an embodiment, hydrogels may be used in the coating for the incorporation of hydrophilic biologically active materials.

Graft coverings may provide for localizing the biologically active material at the ends of a medical device. Graft coverings are strips of fabric such as dacron or expanded PTFE that are used to hold the biologically active material in a matrix. Graft coverings are beneficial to cover the ends of a medical device to prevent abrasion of the device against the vessel wall and scar tissue (anastomotic hyperplasia). Suitable graft coverings include products by Boston Scientific Corporation, Natick, Mass. Alternatively, the "graft" may be sutures or strips attached or interwoven into the ends of the stent, which hold the biologically active material.

In other embodiments, the therapeutics may be distributed throughout the entire length of the medical device. Also, the therapeutics may be distributed evenly or unevenly along the entire length of the medical device. Furthermore, the biologically active material such as genetic materials, may be distributed along the entire length of the medical device in bands leaving some parts of the device without any therapeutics.

Applicable Genetic Materials

One embodiment of the present invention relates to the treatment of restenosis by combining gene therapy approaches with radiation. The combined therapy has a number of benefits: since it has been shown that tissue damage increases the level of gene uptake by cells, radiation treatment is expected to yield analogous results. Gene therapy sensitizes cells to radiation therapy so that the cells are more susceptible to radiation, thereby avoiding the toxic effects of standard intra-arterial radiation.

Genetic materials such as nucleic acid molecules may be delivered via the intravascular route to the site of treatment as an adjunct to radiation treatment. The radiation may be applied using established methods (radioactive wires, balloons, as discussed supra). In a specific embodiment, local delivery of these nucleic acid molecules may be achieved by the use of a catheter placed at the target site for the delivery of genes, carried via a viral or nonviral vector. In one embodiment, radiation treatment as described supra, may be provided prior to, simultaneously with, or subsequent to gene therapy. A stent coated with a nucleic acid may be placed at a treatment site to deliver the nucleic acid in a sustained manner. The benefit of the coated stent would be to eliminate the need for viral vectors.

Still further, in another embodiment, rather than delivering a gene which may have a direct effect on intimal proliferation, it is possible to deliver radiosensitizing agents to reduce restenosis. Since the candy wrapper effect is due to low dose radiation at the ends of an implantable medical device, one embodiment may be to use radiosensitizing agents or genes only at the ends of the implantable medical device and normal doses of radiation in the center. The dosage across the stent may then be homogenized. It is known that the ataxia telangiectasia mutant (ATM) gene is responsible for cell survival following ionizing radiation and that antisense ATM gene therapy has been shown to increase radiosensitivity of tumors. Guha et al., 2000, *Gene Therapy* 7:852–858. In the vasculature, antisense ATM may be delivered either prior to or at the time of radiation to increase susceptibility of the target tissue. In this manner, the cells may be made more susceptible to radiation decreasing the toxic effects commonly observed with intravascular radiation.

Nucleic acids that are useful as biologically active materials for gene therapy in the present invention include, DNA or RNA sequences having a therapeutic effect after being taken up by a cell; antisense DNA and RNA; DNA coding for an antisense RNA; or DNA coding for tRNA or rRNA to replace defective or deficient endogenous molecules. The nucleic acid useful in the invention can also encode for polypeptides. A polypeptide is understood to be any translation product of a polynucleotide regardless of size, and whether glycosylated or not. These polypeptides may include for example, those polypeptides that can compensate for a defective or deficient species in an animal, or those that act through toxic effects to limit or remove harmful cells from the body.

In addition, the polypeptides or proteins that can be incorporated into the medical device used in the present invention, or whose DNA can be incorporated, include without limitation, angiogenic factors including acidic and basic fibroblast growth factors, vascular endothelial growth factor, epidermal growth factor, transforming growth factor a and β, platelet-derived endothelial growth factor, platelet-derived growth factor, tumor necrosis factor α, hepatocyte growth factor and insulin like growth factor; growth factors; cell cycle inhibitors, kinase ("TK") and other agents useful for interfering with cell proliferation, including agents for treating malignancies. Still other useful factors, which can be provided as polypeptides or as DNA encoding these polypeptides, include the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. In addition, molecules capable of inducing an upstream or downstream effect of a BMP can be provided. Such molecules include any of the "hedgehog" proteins, or the DNA's encoding them.

Most preferably, gene therapy mediates a therapeutic effect by expressing genes such as thymidine kinase, retinoblastoma, p53, p21, fasL, VEGF, HGF, P16 (INK4a), MTS-1, CDKN2, and others which have demonstrated effectiveness in inhibiting intimal hyperplasia. In one embodiment, the gene is delivered as a nucleic acid comprises a gene that is part of an expression vector that expresses a functional protein or fragment or chimeric protein.

In a preferred embodiment, the nucleic acid comprises an antisense ATM nucleic acid that is part of an expression vector that produces the antisense molecule in a suitable mammalian cell type that requires gene therapy. In particular, such a nucleic acid has a promoter operably linked to the antisense ATM sequence, said promoter being inducible or constitutive, and, optionally, tissue-specific.

Delivery of the nucleic acid into a patient may be either direct, in which case the patient is directly exposed to the nucleic acid or nucleic acid-carrying vector or a delivery complex, or indirect, in which case, cells are first transformed with the nucleic acid in vitro, then transplanted into the patient. These two approaches are known, respectively, as in vivo or ex vivo gene therapy.

In a specific embodiment, the nucleic acid is directly administered in vivo, where it is expressed to produce a nucleic acid molecule. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in biopolymers (e.g., poly-β-1->4-N-acetylglucosamine polysaccharide; see U.S. Pat. No. 5,635,493), encapsulation in liposomes, microparticles, or microcapsules, or by administering it in linkage to a peptide which is known to enter the nucleus, by administering it in linkage to a ligand subject to receptor-mediated endocytosis (see e.g., Wu and Wu, 1987, J. Biol. Chem. 262:4429–4432), etc. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. USA 86:8932–8935; Zijlstra et al., 1989, Nature 342:435–438).

In a specific embodiment, a viral vector that contains the antisense ATM nucleic acid is used. For example, a retroviral vector can be used (see Miller et al., 1993, Meth. Enzymol. 217:581–599). These retroviral vectors have been modified to delete retroviral sequences that are not necessary for packaging of the viral genome and integration into host cell DNA. The antisense ATM nucleic acid to be used in gene therapy is cloned into the vector, which facilitates delivery of the gene into a patient. More detail about retroviral vectors can be found in Boesen et al., 1994, Biotherapy 6:291–302. Other references illustrating the use of retroviral vectors in gene therapy are: Clowes et al., 1994, J. Clin. Invest. 93:644–651; Kiem et al., 1994, Blood 83:1467–1473; Salmons and Gunzberg, 1993, Human Gene Therapy 4:129–141; and Grossman and Wilson, 1993, Curr. Opin. in Genetics and Devel. 3:110–114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Adenoviruses have the advantage of being capable of infecting non-dividing cells. Kozarsky and Wilson, 1993, Current Opinion in Genetics and Development 3:499–503 present a review of adenovirus-based gene therapy. Bout et al., 1994, Human Gene Therapy 5:3–10 demonstrated the use of adenovirus vectors to transfer genes to the respiratory epithelia of rhesus monkeys. Other instances of the use of adenoviruses in gene therapy can be found in Rosenfeld et al., 1991, Science 252:431–434; Rosenfeld et al., 1992, Cell 68:143–155; and Mastrangeli et al., 1993, J. Clin. Invest. 91:225–234. Adeno-associated virus (AAV) has also been proposed for use in gene therapy (Walsh et al., 1993, Proc. Soc. Exp. Biol. Med. 204:289–300.

The form and amount of therapeutic nucleic acid envisioned for use depends on the cancer or hyperplasia, desired effect, patient state, etc., and can be determined by one skilled in the art.

Another approach to gene therapy involves transferring an antisense gene to cells in tissue culture by such methods as electroporation, inotophoresis, fluid pressure, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient, for purpose of expressing the nucleic acid. In this embodiment, the nucleic acid is introduced into a cell prior to administration in vivo of the resulting recombinant cell. Such introduction can be carried out by any method known in the art, including but not limited to transfection, electroporation, inotophoresis, fluid pressure, sonophoresis, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, 1993, Meth. Enzymol. 217:599–618; Cohen et al., 1993, Meth. Enzymol. 217:618–644; Cline, 1985, Pharmac. Ther. 29:69–92). The technique should provide for the stable transfer of the nucleic acid to the cell, so that the nucleic acid is expressible by the cell and preferably heritable and expressible by its cell progeny.

Sources of Cryotherapy

Cryotherapy is a treatment method that involves cooling targeted body tissue to relatively low temperatures for a period of time which is sufficiently long to inhibit excessive cell proliferation. The mechanism involved in cryotherapy is believed to involve the freezing of the internal cellular matter, expansion of the frozen cellular matter and the consequent rupture of the cell's membranes. In the case of cryotherapy as applied to the surface of a body lumen, the cooling treatment will be directed against all or a portion of a circumferential surface of the body lumen. Such treatment will preferably result in cell growth inhibition, leaving the cells which line the body lumen viable, thus lessening hyperplasia, but not resulting in significant cell necrosis.

In general, during cryotherapy, the temperature at the body lumen surface exposed to the cryotherapy source is in the range from −20° C. to −80° C., preferably from −30° C. to −50° C. The tissue is maintained at such temperatures for a time period in the range from 1 second to 10 seconds, preferably from 2 seconds to 5 seconds. In the case of arteries, the cooling treatment will usually be effected very shortly after angioplasty or other primary treatment procedure, such as radiation, preferably within one hour of the primary treatment, more preferably within thirty minutes within the primary treatment, and most preferably immediately following the primary treatment.

In a preferred embodiment, cryotherapy is applied to the parts of the surface of the body lumen that are in contact with the opposing ends of an implanted medical device. The lumen surface is exposed in the cryotherapy source for a time sufficient to inhibit subsequent cell growth for the treatment of restenosis or hyperplasia.

Cryotherapy sources include thermoelectric coolers, peltier effect coolers, ultrasound, high pressure gas, liquid nitrogen or other cold fluids. See U.S. Pat. No. 6,241,718 B1. Other cryogenic fluid sources are described in U.S. Pat. Nos. 5,644,502; 5,617,739; and 4,336,691. The use of ultrasonic freeze to kill cells is described in U.S. Pat. No. 5,139,496.

The device with which cryotherapy is generally applied includes catheters, such as balloon catheters, that are known in the art. Balloon catheters for intravascularly cooling or heating a body lumen are described in U.S. Pat. No. 5,486,208 and WO 91/05528. In one embodiment the catheter comprises a lumen for delivering the cryotherapy source, such as a cold fluid. The cryotherapy source is delivered directly to the parts of the surface of the body lumen that are in contact with the opposing ends of the medical device to freeze the cells in those areas.

Another embodiment of a suitable balloon catheter is illustrated in FIG. 4. The balloon catheter comprises a lumen 210, used in delivering a cryotherapy source, which is in fluid connection with the inside of the balloon. The cryotherapy source is placed in the balloon through the lumen 210. In another embodiment, there may be more than one balloons in conjunction with the medical device. Along the lumen 210, there are openings for the cryotherapy source to enter and inflate the balloon 190. These openings 200 are positioned in such a way that they are near the surface of the body lumen that are in contact with the opposing ends of the medical device. As the balloon 190 is inflated, the outer wall of the balloon contacts those parts of the surface of the body lumen that are in contact with the opposing ends of the medical device. Since the openings 200 along the catheter 140 are near the ends of the medical device, the balloon near both ends of the medical device has the lowest temperature and the temperature increases toward the center of the balloon. The cryotherapy source, such as liquid nitrogen, will serve both to inflate the balloon and to cool the exterior surface of the balloon to a desired temperature profile. In a specific embodiment, more than one balloon may be used in an apparatus.

It will be appreciated that the treatment region of the balloon can be varied considerably by varying the length of the balloon and controlling the volume of the cryotherapy source, placed in the balloon. In general, the balloon has a working length of up to 25% of the length of the implantable medical device. Exemplary balloons will have a length in the range from about 3 cm to 5 cm, a diameter in the range from about 1.5 mm to 4 mm, and will typically receive from about 0.08 ml/sec to 1.5 ml/sec of a cryotherapy source. The treatment is localized at parts of the surface of the body lumen that are in contact with the opposing ends of a medical device to reduce injuries to healthy cells along the surface of the body lumen. After a predetermined time passes, the balloon catheter is deflated and removed from the body lumen. The time during which the balloon is inflated should be determined by the type of body lumen tissue and the type of cryotherapy used. One skilled in the art may determine the best placement of the openings 200 along the catheter 140 with respect to the surface of the body lumen that are in contact with the opposing ends of the medical device. Preferably, the opening 200 along the cryogenic delivery tube is about 1 cm away from either end of the medical device.

Also suitable are cryosurgical probes that are cooled using very high pressure gas which undergoes expansion through a Joule-Thomson valve. Such probes are described in U.S. Pat. Nos. 5,275,595; 5,190,539; 5,147,355; 5,078,713; and 3,901,241. Furthermore, a cryosurgical probe with an inflatable bladder for performing intrauterine ablation which is described in U.S. Pat. No. 5,501,681 is also suitable.

Sources of Thermotherapy

Thermotherapy or heat treatment is a treatment method where various energy sources are applied to tissues in order to cause the cells to shrink and tighten or to denature the structural proteins. This treatment is often less traumatic than surgical procedures. Heat treatment has the advantage of using an energy source that is easily obtained, easily controlled. The source of heat is easily obtained and controlled such as from a hot wire, hot fluids, ultrasound, laser etc. The energy source is rapidly dissipated and reduced to a non-destructive level by conduction and convection.

In the present invention, thermotherapy is applied specifically to the parts of the surface of the body lumen that are in contact with the opposing ends of an implanted medical device at a temperature and for a time sufficient to inhibit subsequent undesired cell growth, such as restenosis or hyperplasia.

Suitable thermotherapy sources include ultra-violet rays, ultrasonic energy, x-rays, radio frequency energy, heated fluids, electrical current, microwave energy, electrical pulses, light energy such as lasers, tissues destructive substances or other kinds of hyperthermic energy. Preferably, the thermotherapy source is a radio frequency energy that exposes a patient to minimal side effects and risks.

In thermotherapy, heat is generated by a suitable energy source. The heat is then applied to the body tissue by devices that typically include a catheter, which is used to carry a radio frequency electrode, microwave energy antenna or a resistance wire, to the area of treatment, and applying energy to the interior surface of a lumen. The proximal terminal end of the catheter can be connected to a radio frequency distributor which is connected to a radio frequency generator.

Specifically, the invention may include the use of photodynamic therapy, which involves the use of a biologically active material that can be activated or triggered, for example by energy, to kill cells.

Any suitable medical device may be used to apply the thermotherapy source to a body lumen as determine by one skilled in the art. For example, a catheter may be introduced near the tissue in contact with the ends of an implanted medical device. Such catheter may have a lumen for applying or dispensing the thermotherapy source which is similar to the balloon catheter that is used in cryotherapy as described supra. Catheters with heated balloons for post-angioplasty and other treatments are useful. These balloons are described in U.S. Pat. Nos. 5,196,024; 5,191,883; 5,151,100; 5,106,360; 5,092,841; 5,041,089; 5,019,075; and 4,754,752.

Thermotherapy for the retardation of cell proliferation requires a temperature of approximately 50° C. It is preferred to heat tissue to 50° C. up to 5 mm from the catheter axis. At 100° C., undesirable charring and desiccation takes place.

Other materials that may be set off or activated, such as the use of resistance heating, and hot fluids in catheter or balloon which spray hot fluids to generate heat. These heat sources may be incorporated to opposing ends of a medical device.

Methods of Making the System of the Invention

The present invention is directed to a method of making a system for delivering a biologically active material to a surface of a body lumen that is exposed to a radioactive source. The system comprises an implantable medical device and a radioactive source. The method comprises obtaining an implantable medical device that has two opposing ends having a surface and a middle portion. The radioactive source can be provided by making the medical device from a radioactive material or placing a radioactive material inside the medical device. Alternatively, a coating containing a radioactive material may be applied on the surface of the medical device. Also, the medical device can be made of a non-radioactive material which is later irradiated.

The biologically active material is incorporated in the opposing ends of the medical device, which is the portion at the terminal ends of the device, each end is no more than 25% of the total length of the device. The biologically active material can be incorporated as a coating as discussed above or by any other method known to the skilled artisan. Also, the middle portion of the device is kept free of biologically active material.

The present invention further provides a method for making a system for delivery of a genetic material to a surface of a body lumen exposed to a radioactive source. The system comprises an implantable medical device having a surface. This method comprises providing a radioactive source and incorporating a genetic material in the medical device. The genetic material may be incorporated onto the surface of the entire length of the medical device or only in certain parts of the device.

The present invention also provides a method for making a system for treating a surface of a body lumen with a biologically active material and a cryotherapy or thermotherapy source. The system comprises an implantable medical device and a device for delivering the cryotherapy or thermotherapy source. This method comprises obtaining an implantable medical device that has two opposing ends with a surface and a middle portion. The opposing ends are capable of being placed in contact with at least a part of the body lumen surface. A biologically active material is applied to the medical device, such as by applying a coating with the biologically active material onto the surface of the medical device. The device for delivering the cryotherapy or thermotherapy to the surface of the body lumen that is in contact with the ends of the medical device include a balloon catheter.

Also, the present invention provides a method for making a system for treating a surface of a body lumen exposed to a radioactive source and a cryotherapy or thermotherapy source. Such system comprises a medical device and device for delivering the cryotherapy or thermotherapy source. The method comprises obtaining an implantable medical device that has two opposing ends with a surface and a middle portion. The opposing ends of the device are capable of being placed in contact with at least a part of the body lumen surface. A radioactive source is provided by, inter alia, making the medical device using a radioactive material, exposing the device to radiation prior to surgery, or placing a radioactive material inside the medical device. One of ordinary skill in the art is aware of suitable radioactive sources. The device for delivering the cryotherapy or thermotherapy source to the surface of the body lumen that is in contact with the ends of the medical device can include a catheter.

Use of System for Treating Body Lumina

One method of treating the body lumina, which has been irradiated with a radioactive source, is that the medical device of a system of the present invention is inserted into a body lumen where the opposing ends of the medical device are in contact with at least a part of the body lumen surface. Insertion of the medical device may be done by any well-known percutaneous insertion techniques as determined by one skilled in the art. When the system is a self-expandable stent having two opposing ends which are coated with a biologically active material, the expandable portion of the stent is subsequently expanded to bring the biologically active material on the coating of the medical device into contact with the surface of the body lumen that is in contact with the opposing ends of the stent. The biologically active material is released from the coating as it slowly dissolves into the aqueous bodily fluids. The biologically active material may be release through diffusion or pressure (similar to release from a sponge). This enables administration of the biologically active material to be site-specific, limiting the exposure of the rest of the body to the biologically active material.

Another method of treating the body lumina requires the insertion of the medical device of another system of the present invention into a body lumen where the medical device is coated with a biologically active material. The medical device is placed in the lumen such that the medical device are in contact with at least a part of the body lumen surface. A therapy source, either cryotherapy or thermotherapy, is applied to the part of the body lumen surface that is in contact with the medical device through a catheter. The therapy is directed to the part of the body lumen surface where restenosis or hyperplasia is most likely to occur. In a specific embodiment, the therapy source is applied to the lumen surface that are in contact with the opposing ends of the medical device.

In an embodiment, the method of treatment uses a system, which comprises an implantable medical device, for delivering a biologically active material to a surface of a body lumen being exposed to a radioactive source. Neither the source of the biologically active material nor the source of the radiation are part of the implantable medical device. In one embodiment, the method utilizes radiation source that is provided by a radioactive wire that is placed in the center of the implantable medical device. The biologically active material is provided through a balloon which may be located along the entire length of the implantable medical device. In another embodiment, the method utilizes biologically active material that is provided through a balloon located at the ends of the implantable medical device.

Another method of treating the body lumina requires the insertion of the medical device of another system of the present invention into a body lumen which has been exposed or is exposed to a radioactive source. The medical device is inserted into a body lumen such that the opposing ends of the medical device are in contact with at least a part of the body lumen surface. A therapy source, either cryotherapy or thermotherapy, is applied to the part of the body lumen surface that is in contact with the opposing ends of the medical device through a catheter. The therapy is directed to the part of the body lumen surface where restenosis or hyperplasia is most likely to occur.

The present invention provides a method of treatment to reduce or prevent the degree of restenosis or hyperplasia after vascular intervention such as angioplasty, stenting, atherectomy and grafting. All forms of vascular intervention are contemplated by the invention, including, those for treating diseases of the cardiovascular and renal system. Such vascular intervention include, renal angioplasty, percutaneous coronary intervention (PCI), percutaneous transluminal coronary angioplasty (PTCA); carotid percutaneous transluminal angioplasty (PTA); coronary by-pass grafting, angioplasty with stent implantation, peripheral percutaneous transluminal intervention of the iliac, femoral or popliteal arteries, carotid and cranial vessels, surgical intervention using impregnated artificial grafts and the like. Furthermore, the system described in the present invention can be used for treating vessel walls, portal and hepatic veins, esophagus, intestine, ureters, urethra, intracerebrally, lumen, conduits, channels, canals, vessels, cavities, bile ducts, or any other duct or passageway in the human body, either in-born, built in or artificially made. It is understood that the present invention has application for both human and veterinary use.

The present invention also provides a method of treatment of diseases and disorders involving cell overproliferation, cell migration, enlargement. Diseases and disorders involving cell overproliferation that can be treated or prevented include but are not limited to malignancies, premalignant conditions (e.g., hyperplasia, metaplasia, dysplasia), benign tumors, hyperproliferative disorders, benign dysproliferative disorders, etc. that may or may not result from medical intervention. For a review of such disorders, see Fishman et al., 1985, *Medicine*, 2d Ed., J. B. Lippincott Co., Philadelphia.

Accordingly, the present invention provides method of treatment of various types of cancers and solid tumors including, but not limited to, sarcomas, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, thyroid carcinomas, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, bladder carcinoma, epithelial carcinoma glioma, glioblastoma, astrocytoma, medulloblastoma, craniopharyngioma, ependymoma, pinealoma, hemangioblastoma, acoustic neuroma, oligodendroglioma, menangioma, neuroblastoma, and retinoblastoma.

In a preferred embodiment, the present invention provides a method of treatment for renal cell cancer, also known as kidney cancer or renal adenocarcinoma, a disease in which cancer cells are found in the tubules of the kidney. Accordingly, a preferred embodiment of the method of the present invention is the implantation of the system of the present invention in the tubules of the kidney for the treatment of renal cell cancer.

In another preferred embodiment, the present invention provides a method of treatment for prostate cancer. Other treatments of cancer may be used in combination with the treatment method of the present invention. These other treatments of cancer include, without limitation, surgery, chemotherapy, radiation therapy, hormonal therapy and biological therapy (biological response modifier therapy or immunotherapy).

In particular, the method of the invention used to treat or prevent hyperplasia may be administered in conjunction with one or a combination of chemotherapeutic agents including, but not limited to, methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, campathecins, bleomycin, doxorubicin, idarubicin, daunorubicin, dactinomycin, plicamycin, mitoxantrone, asparaginase, vinblastine, vincristine, vinorelbine, paclitaxel, and docetaxel. In a preferred embodiment, the medical device that is used in the present invention is coated with a chemotherapeutic agent or other type of toxin (e.g., a ricin toxin, or a radionuclide, or any other agent able to kill cancerous cells or to arrest cell growth). In another preferred embodiment, the chemotherapeutic agents can be activated by a radiation source that is provided in the system of the present invention.

Many cancer cells are resistant to initial chemotherapeutic treatment or will eventually develop resistance to a chemotherapeutic agent. Some cancers respond poorly to treatment methods such as chemotherapy and radiation therapy (Boring et al., 1994, Cancer J. Clinic. 44: 7–26). As such, there is a need of sensitizing cancer cells so that these cells will be more receptive to treatment which improves treatment outcomes. When chemotherapeutic agents such as cisplatin, busulfan, temozolomide, and procarbazine are used to treat cancer, the varying degree of resistance of cancer cells to these drugs has been shown to produce a large difference in clinical responsiveness in vivo as demonstrated in tumor model systems.

The present invention can be used to sensitize overproliferative cells to chemotherapeutic and radiation. Accordingly, preferably the present invention provides methods for sensitizing overproliferative cells such as cancer cells to chemotherapy or radiation therapy using drugs such as taxol. For example (as mentioned supra), a sensitizing agent at the ends of the medical device may allow those areas to absorb radiation in a more evenly distributed manner, leading to an abatement of restenosis.

Assessment of Efficacy of Treatments

Whether a particular treatment of the invention is effective to treat restenosis or hyperplasia of a body lumen can be determined by any method known in the art, for example but not limited to, those methods described in this section.

The safety and efficiency of the proposed method of treatment of a body lumen may be tested in the course of systematic medical and biological assays on animals, toxicological analyses for acute and systemic toxicity, histological studies and functional examinations, and clinical evaluation of patients having a variety of indications for restenosis or hyperplasia in a body lumen.

The efficacy of the method of the present invention may be tested in appropriate animal models, and in human clinical trials, by any method known in the art. For example, the animal or human subject may be evaluated for any indicator of restenosis or hyperplasia in a body lumen that the method of the present invention is intended to treat. The efficacy of the method of the present invention for treatment of restenosis or hyperplasia can be assessed by measuring the size of a body lumen in the animal model or human subject at suitable time intervals before, during, or after treatment. Any change or absence of change in the size of the body lumen can be identified and correlated with the effect of the treatment on the subject. The size of the body lumen can be determined by any method known in the art, for example, but not limited to, angiography, ultrasound, fluoroscopy, magnetic resonance imaging, optical coherence tumography and histology.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various references are cited herein, the disclosure of which are incorporated by reference in their entireties.

We claim:

1. A system for delivering a biologically active material to a surface of a body lumen exposed to a radioactive source comprising:
   (a) an implantable medical device having two opposing ends, a middle portion and a surface; and
   (b) at least one biologically active material applied to the ends of the medical device,
   wherein the middle portion is substantially free of any biologically active material; and
   wherein the biologically active material comprises a non-genetic therapeutic agent, a genetic material, a cell or a charged therapeutic agent, and is in a particulate form having an average particle size of about 1 to about 100 microns.

2. A system for delivering a biologically active material to a surface of a body lumen exposed to a radioactive source comprising:
   (a) an implantable medical device having two opposing ends, a middle portion and a surface;
   (b) a biologically active material incorporated into a first coating composition; and
   (c) a second coating composition comprising a second biologically active material, wherein the first and the second coating composition are disposed upon at least one end of the medical device; and the middle portion is substantially free of a biologically active material.

3. The system of claim 2 further comprising a radioactive source for delivering radiation to the surface of the body lumen.

4. The system of claim 1 further comprising a radioactive source for delivering radiation to the surface of the body lumen.

5. A system for delivering a biologically active material to a surface of a body lumen exposed to a radioactive source comprising:
   (a) an implantable medical device having two opposing ends, a middle portion and a surface; wherein the medical device comprises a catheter, a guide wire, a balloon, a filter, a stent, a stent graft, or a vascular graft; and
   (b) at least one biologically active material applied to the ends of the medical device; wherein the biologically active material is released upon application of the radioactive source, and wherein the middle portion is substantially free of any biologically active material.

6. The system of claim 5 wherein the device is a stent.

7. The system of claim 6 wherein the stent comprises a radioactive material.

8. The system of claim 5 further comprising a catheter for applying the radioactive source.

9. The system of claim 5 wherein the biologically active material is incorporated into a first coating composition and wherein the first coating composition is applied to at least one end of the medical device.

10. The system of claim 5 wherein the biologically active material comprises a non-genetic therapeutic agent, a genetic material, a cell or a charged therapeutic agent.

11. The system of claim 10 wherein the biologically active material comprises a glucocorticoid, heparin, hirudin, angiopeptin, aspirin, an ACE inhibitor, a growth factor, an oligonucleotide, an antiplatelet agent, an anti-hypertensive, an anti-coagulant agent, an antimitotic agent, an antioxidant, an antimetabolite agent, an anti-inflammatory agent or an antibiotic.

12. The system of claim 10 wherein the biologically active material comprises paclitaxel.

13. The system of claim 5 wherein the lengths of the two opposing ends of the medical device are each about 1–25% of the full length of the medical device.

14. The system of claim 13 wherein the lengths of the two opposing ends of the medical device are each about 5–15% of the full length of the medical device.

15. The system of claim 5 further comprising a radioactive source for delivering radiation to the surface of the body lumen.

* * * * *